United States Patent
Andrawes et al.

(10) Patent No.: US 11,047,837 B2
(45) Date of Patent: Jun. 29, 2021

(54) MOBILE INTEGRATED DEVICE AND ELECTRONIC DATA PLATFORM FOR CHEMICAL ANALYSIS

(71) Applicant: Green Ocean Sciences, Inc., Austin, TX (US)

(72) Inventors: Alexander Fayek Andrawes, Austin, TX (US); David Cree Crawford, Fair Oaks Ranch, TX (US); Craig Fontenot, Austin, TX (US); Quan Shi, West Roxbury, MA (US)

(73) Assignee: Green Ocean Sciences, Inc., Austin, TX (US)

( * ) Notice: Subject to any disclaimer, the term of this patent is extended or adjusted under 35 U.S.C. 154(b) by 255 days.

(21) Appl. No.: 16/123,559

(22) Filed: Sep. 6, 2018

(65) Prior Publication Data

US 2019/0072529 A1    Mar. 7, 2019

Related U.S. Application Data

(60) Provisional application No. 62/554,951, filed on Sep. 6, 2017.

(51) Int. Cl.
*G06F 11/30* (2006.01)
*G01N 30/86* (2006.01)
(Continued)

(52) U.S. Cl.
CPC ..... *G01N 30/8675* (2013.01); *G01N 30/8651* (2013.01); *G01N 33/0075* (2013.01);
(Continued)

(58) Field of Classification Search
CPC .................................................. G01N 30/8675
See application file for complete search history.

(56) References Cited

U.S. PATENT DOCUMENTS 9,832,089 B2   4/2017   Jackson, Jr.
10,222,361 B2   3/2019   Jackson, Jr.
(Continued)

OTHER PUBLICATIONS

International Search Report and Written Report issued for PCT Application No. PCT/US2018/049721, dated Nov. 6, 2018, 11 pages.

*Primary Examiner* — Phuong Huynh
(74) *Attorney, Agent, or Firm* — Sprinkle IP Law Group

(57) ABSTRACT

Systems, methods and computer program products for cannabis analysis, such as a system that has a cannabis analysis data server and a plurality of mobile cannabis analysis devices that are communicatively coupled to a network. The mobile devices perform physical analyses of a physical sample and communicate resulting data to the cannabis analysis data server with a unique identifier. The mobile cannabis analysis devices may also monitor device and external environmental conditions that affect the performance and communicate these to the cannabis analysis data server. The cannabis analysis data server performs analyses on the received data from the mobile devices. Based on the sample analyses, the cannabis analysis data server generates sample analysis reports and communicates them to a user. The cannabis analysis data server may also generate data to control the operation of the mobile cannabis analysis devices based on the operation and environmental data received from the devices.

14 Claims, 11 Drawing Sheets

(51) Int. Cl.
*G01N 33/00* (2006.01)
*G01N 30/00* (2006.01)
*G01N 30/88* (2006.01)

(52) U.S. Cl.
CPC . *G01N 33/0098* (2013.01); *G01N 2030/0095* (2013.01); *G01N 2030/8804* (2013.01)

(56) References Cited

U.S. PATENT DOCUMENTS

| | | | |
|---|---|---|---|
| 2002/0118355 A1* | 8/2002 | Worthington | G16H 10/40 356/72 |
| 2003/0004679 A1 | 1/2003 | Tryon, III et al. | |
| 2007/0067142 A1* | 3/2007 | Kavaklioglu | G06F 3/0482 702/182 |
| 2008/0229805 A1* | 9/2008 | Barket | G01N 1/2214 73/31.01 |
| 2019/0195852 A1 | 6/2019 | Bryant | |

* cited by examiner

LOADING SAMPLE

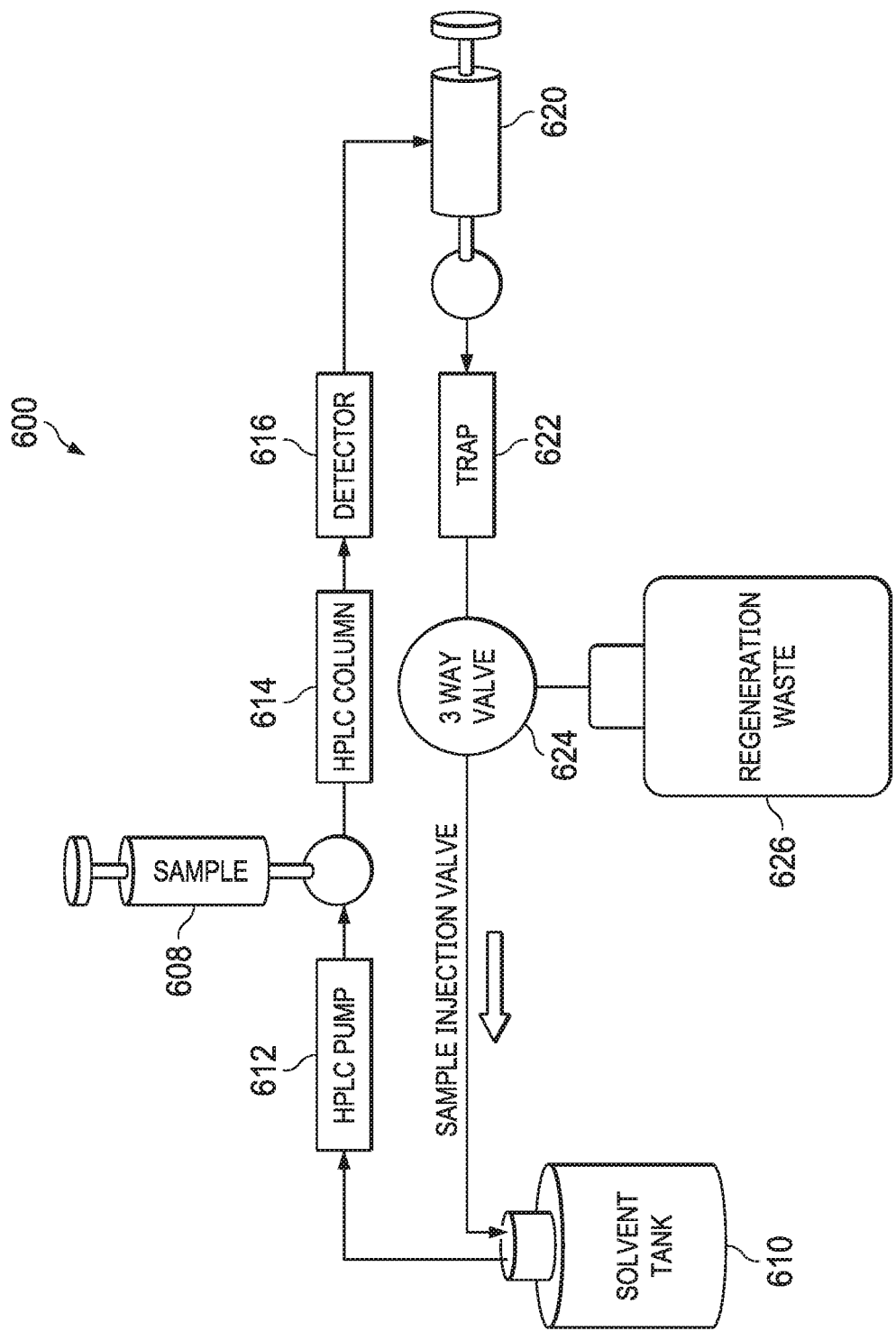

MOBILE INTEGRATED DEVICE AND ELECTRONIC DATA PLATFORM FOR CHEMICAL ANALYSIS

CROSS-REFERENCE TO RELATED APPLICATIONS

This application claims the benefit of U.S. Provisional Patent Application 62/554,951, filed Sep. 6, 2017, which is incorporated by reference as if set forth herein in its entirety.

COPYRIGHT NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

BACKGROUND

There are believed to be well over 400 different naturally occurring chemical compounds found in cannabis. Of these it is thought that approximately 80 are cannabinoids, approximately 140 are terpenoids with the balance being cannabigerols, cannabichromenes, nitrogenous compounds, amino acids, and ketones, among others. These are thought to act together in a synergistic way, known as the 'entourage effect'.

Current processes for analyzing cannabis samples utilize independent analytical devices that perform physical tests or analyses on the samples. Examples of these devices include, but are not limited to: PID (photo ionization detector), GC-PID (gas chromatograph photo ionization detector), GC-FID (gas chromatograph flame ionization detector), GC-MS gas chromatograph mass spectrometer), HPLC (high performance liquid chromatography), IMS, DMS, and other light-based spectrometers such as FTIR, NIR, Deep-UV, UV-Vis, UV Fluorescence, Raman, XPS, XRF, LIBS, etc. While some prior less expensive measurement solutions, such as NIR and z-nose (electronic nose) have been used in an attempt to measure cannabinoids and/or other chemicals, they have not delivered analytical grade results. Thus, multiple different types of chemical analytical devices must be used, each designed, manufactured, and operated individually.

Current solutions for analyzing the chemical compounds found in a cannabis sample are unsatisfactory because they are immobile, expensive, unwieldy and difficult to operate. For example, the direct analysis of both cannabinoids and terpenes is done on two different types of devices. Currently, the individual chemical analytical devices are most often benchtop, but some have been redesigned to be mobile. Whether benchtop or mobile, each individual device is maintained in a separate single physical enclosure and the software for each device is separate and run on each local device. The devices are independently operated and are not designed to run in parallel and/or tandem with other chemical analytical devices under an integrated control process. Because the devices are independently operated, it may also be difficult to ensure the precision and accuracy of the devices (e.g., with respect to similar devices).

For example, gas chromatography is effective for non-reactive volatile compounds and is the gold standard for detecting and quantifying terpenes and residual solvents but is not readily capable of detecting the more reactive compounds of interest (i.e. the cannabinoid acids THCa, CBDa, CBCa, CBGa, CBNa, CBLa, and others) directly (without additional sample preparation i.e., derivitization). Liquid chromatography is the gold standard for detecting and quantifying the cannabinoid acids directly but has limited utility for more volatile compounds such as terpenoids, residual solvents, etc.

Additionally, current devices run in a local environment, that is, at most their internet connectivity is limited to a local intranet environment maintained by the end customer, or an occasional internet session for troubleshooting. Thus, with current solutions, the chemical analysis and related metadata, if any, is compartmentalized and privately stored at each location. Further, because the devices are independent, analysis of samples is dependent upon variables that may fluctuate independently from one device to another, so it may be difficult to produce consistent, precise, accurate and verifiable test results. Still further, a given cannabis sample must conventionally be analyzed in a laboratory, or on various independent mobile devices. In either case, the sample results acquired from each device must be sorted, collated and combined into a single report, which may allow the test results to be manipulated or changed, either intentionally or accidentally.

SUMMARY

This disclosure is directed to systems and methods that solve one or more of the problems discussed above using mobile integrated devices and an electronic data platform for chemical analysis. One particular embodiment comprises a chemical analysis data system that includes a chemical analysis data server and a plurality of mobile chemical analysis devices that are remote from the chemical analysis data server. The chemical analysis data server and the mobile chemical analysis devices are communicatively coupled to a network. The mobile chemical analysis devices are adapted to perform physical analyses of a physical sample (e.g., photo ionization analysis, gas chromatograph ionization analysis, gas chromatograph mass spectrometry, liquid chromatography, etc.) and to communicate data resulting from the physical analyses to the chemical analysis data server. Each mobile chemical analysis device may generate a unique identifier for each sample it processes, where the unique identifier is communicated to the chemical analysis data server with the data resulting from the physical analyses. The chemical analysis data server is adapted to perform sample analyses on the data received from the mobile chemical analysis devices (e.g., identifying or matching chemotypes, determining correlations between phenotype, genotype and chemotype, etc). Based on the sample analyses, the chemical analysis data server generates sample analysis reports (e.g., chemical signature reports, etc.) and communicates the sample analysis reports to a user.

In one embodiment, each of the mobile chemical analysis devices incorporates multiple analytical device modules that are adapted to analyze a physical sample, where each of the analytical device modules performs a distinct type of sample analysis on the physical sample. Each of the mobile chemical analysis devices may also be adapted to monitor their own device parameters or other conditions associated with the device (e.g., environmental parameters) and to communicate this information to the chemical analysis data server, which may aggregate the device parameters and perform one or more analyses on the aggregated device parameters. In one embodiment, the chemical analysis data server is adapted to perform multivariate analysis on the aggregated device parameters and to identify a fault condition of one of the mobile chemical analysis devices which is indicated by a corresponding parameter which is determined to be outside an acceptable range for the parameter based on the multivariate analysis of the aggregated device parameters.

In one embodiment, the mobile chemical analysis devices may have a user interface which is co-located with the mobile chemical analysis device. The user interface may be adapted to enable input of user-provided metadata associated with a sample. The user-provided metadata may then be communicated by the mobile chemical analysis device to the chemical analysis data server along with the data resulting from the physical analyses. The user interface may also be adapted to receive data from the chemical analysis data server defining user instructions for preparing the physical sample, or taking one or more actions to operate the mobile chemical analysis device. The mobile chemical analysis devices may therefore be capable of walking users through the procedures for operating the device, step-by-step.

One alternative embodiment comprises a method for implementing the functions of the chemical analysis data system described above. Another alternative embodiment comprises a computer program product in which a non-transitory computer readable medium stores instructions that are translatable by a computing device to implement a chemical analysis data system as described above. Numerous other embodiments are also possible.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. Note that the features illustrated in the drawings are not necessarily drawn to scale.

DESCRIPTION

Figure 1:
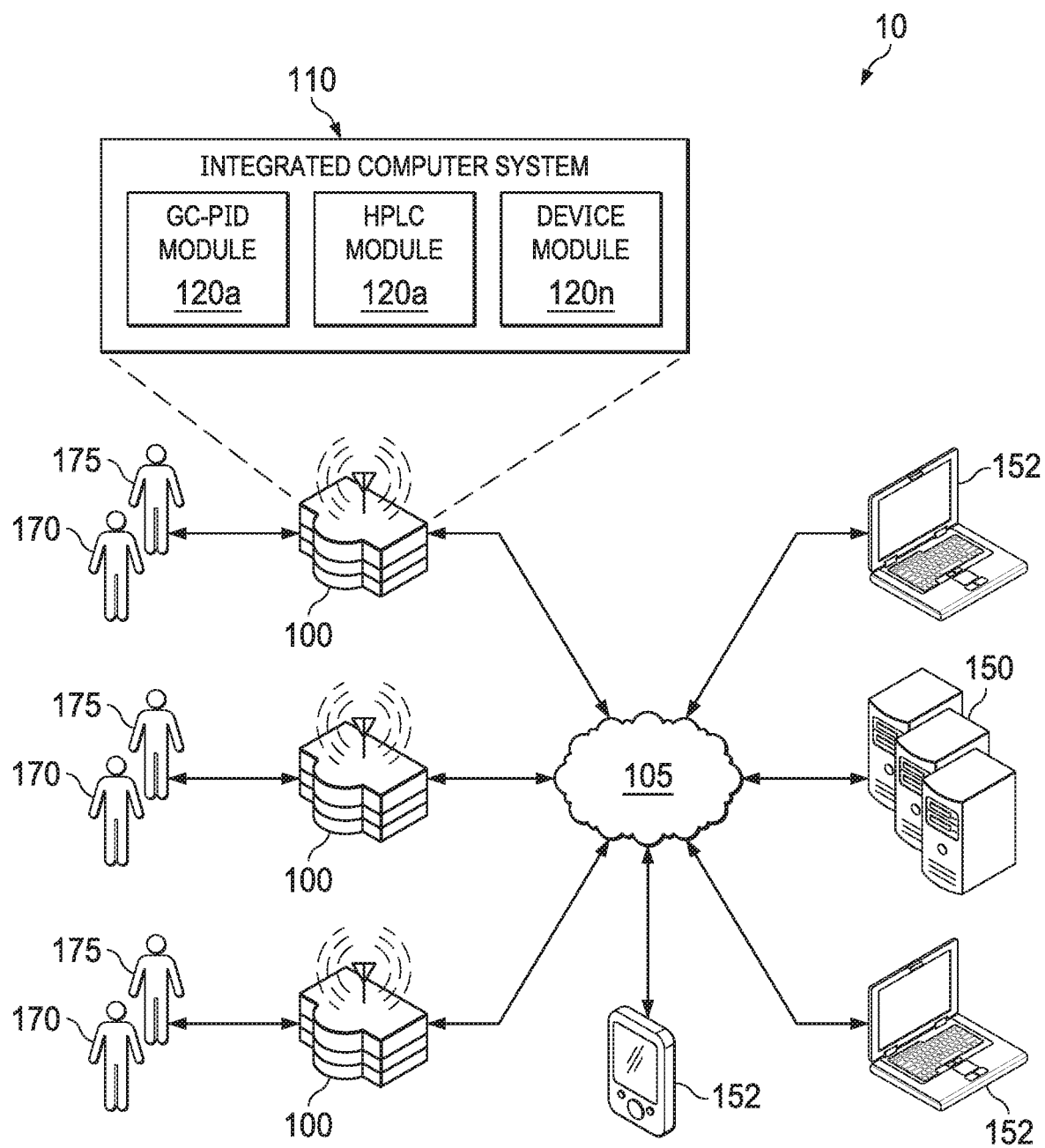
FIG. 1 is a diagrammatic representation of one embodiment of a chemical data analysis system.

Various embodiments of the disclosure are illustrated in the FIGURES, like numerals being generally used to refer to like and corresponding parts of the various drawings. Embodiments of the disclosure provide systems and methods for regenerating cached pages. Descriptions of well-known starting materials, processing techniques, components and equipment are omitted so as not to unnecessarily obscure the invention in detail. It should be understood, however, that the detailed description and the specific examples, while indicating preferred embodiments of the systems and methods, are given by way of illustration only and not by way of limitation. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having" or any other variation thereof, are intended to cover a non-exclusive inclusion. For example, a process, article, or apparatus that comprises a list of elements is not necessarily limited only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Language designating such nonlimiting examples and illustrations includes, but is not limited to: "for example", "for instance", "e.g.", "in one embodiment".

Physical chemical analysis devices and networked management and analysis platforms are provided. The devices and platform can include technique(s) for mobile and/or remote chemical analysis, end-user data collection, metadata aggregation, data analysis and a reporting platform.

Embodiments described herein may utilize a mobile chemical analysis device that includes multiple analytical devices contained in a single portable mobile enclosure and software that is capable of running the analytical devices in parallel or in series. According to one embodiment, a mobile chemical analysis device uses multiple chromatographic and/or multiple spectroscopic techniques in order to provide a single mobile device for analysis of many diverse constituent chemicals of a sample. For example, one embodiment of a mobile chemical analysis device may include both gas chromatography and liquid chromatography in a single enclosure. The mobile chemical analysis device may be ruggedized, have a small form factor and utilize both AC and DC battery power.

In particular, with the growing interest, medical and otherwise, in characterizing the cannabis plant, cannabis flower, cannabis extract and cannabis infused products, the mobile chemical analysis device will be used to analyze cannabis. For purposes of this disclosure, a cannabis sample may include a sample of a cannabis containing substance, including, but not limited to, marijuana plant sample or marijuana infused product (MIPs) sample. The mobile analysis devices and platform can provide a comprehensive mobile cannabis testing solution for cannabinoids, terpenoids and other chemicals in a cannabis sample that can meet the testing requirements for the cannabis industry. For example, a mobile chemical analysis device can be adapted to analyze the entire cannabis chemotype (both cannabinoids and terpenoids) directly without chemical derivitization and or cannabinoid acid conversion to parent cannabinoid compound. A mobile chemical analysis device may be further adapted to detect the presence of various other substances.

It should be noted that, while the exemplary embodiments herein are described primarily in relation to the testing of cannabis samples (e.g., samples of marijuana plants or MIPs), these and other embodiments may be used to test other substances. In particular, it is contemplated that they are useful in the testing of hemp samples. Hemp samples, for example, may be tested to ensure that particular chemicals such as THC are not present (in contrast to the testing of cannabis samples, where positive levels of THC are expected).

According to one embodiment, the mobile chemical analysis device is designed for a lay-person to operate. A user interface may be provided that allows a user to select from a menu of chemical tests important to the cannabis industry including but not limited to: potency (cannabinoids) and/or terpenes. The system can return results quickly (less than 60 minutes and in some cases less than 5 minutes) depending on the suite of analytical tests run.

The mobile chemical analysis device may be designed to be very affordable. As such, customers can justify more testing before selling/purchasing, during cultivation, during processing (process control) and as internal QC/QA during/after the extraction/infusion processes.

Embodiments may leverage end-user real-time chemical analysis data collection, platform-based data collection, platform based analytics, other related metadata collection, data aggregation, or big datamining approaches/techniques to analyze, synthesize and understand the nature of the structured and unstructured data.

A plurality of mobile chemical analysis devices may be connected to a remote data platform that provides various analyses and reporting. "Remote" is used here to indicate that the mobile chemical analysis devices and the data platform or server are not co-located, but are physically separated by some distance. The data platform can provide chemical library updates for new chemicals of interest, machine learning and/or computer science approaches to collect chemical data, analyze the chemical data, user reported metadata and other metadata in near real-time, and deliver advanced analytics results. According to one embodiment, the data platform may be a cloud-based platform.

Some embodiments can provide one or more of the following: remote chemical library updates; auto-calibration validation; auto device performance monitoring (tuning, baseline drift, detector shift, damage caused by drops/impacts); tracking of number of tests; real-time machine learning based data analysis and advanced analytics reporting; geofencing of allowed areas for device to be defined and limited; ability to turn device on/off remotely; ability to troubleshoot device remotely.

Embodiments described herein may collect a rich set of data at the time a sample is tested. In addition, the data platform may receive test data and accompanying data for a large number of sample tests from any number of mobile chemical analysis devices. Thus, the results of a particular test may be compared to chemical libraries determined from a large number of tests.

FIG. 1 is a diagrammatic representation of one embodiment of a chemical data analysis system 10 comprising a plurality of mobile analysis devices 100 connected to a central chemical analysis data server 150 via a network 105 comprising a local area network (LAN), wide area network (WAN), the internet, cellular network and or other wired and/or wireless network. Any suitable data transfer protocols may be used. According to one embodiment, a mobile analysis device 100 includes Wi-Fi or cellar data connection capability. In some embodiments, data can be transferred to a mobile phone via Bluetooth or Wi-Fi and the phone used to send data to chemical analysis data system. A mobile analysis device may also include a cellular adapter.

Each mobile analysis device 100 may comprise an integrated computer system 110 having one or more central processing units executing instructions embodied on one or more computer readable media where the instructions are configured to perform at least some of the functionality associated with embodiments of the present invention. The integrated computer system 110 may include one or more user interface devices, network interface devices and other computer components.

A mobile chemical analysis device 100 can comprise one or more analytical devices to implement a variety of chemical analysis techniques. The analytic devices may be miniaturized and modularized, with each analytical device enclosed in small self-contained analytical device module 120 with the modules 120 positioned physically adjacent to each other. Multiple analytical device modules 120 may be combined and integrated into a single, mobile, battery and/or AC operated enclosure.

The analytical device modules 120 of a mobile chemical analysis device 100 may share hardware resources (e.g., PCB's, components, microprocessors, memory, display, pumps or other hardware resources) and software resources. In one embodiment, for example, each analytical device module 120 may be connected to a shared control board, a shared power supply, shared communication method and/or other shared resources and a combination a combination of module specific and shared software controls the analytical device modules 120. Integrated computer 110 may provide a shared communication method to communicate with chemical analysis data server 150 via network 105.

Analytical device modules 120 may include a variety of analytical devices in a single housing, including but not limited to: PID, GC-PID, GC-FID, GC-MS gas chromatograph mass spectrometer), HPLC, IMS, DMS, and other light-based spectrometers such as FTIR, NIR, Deep-UV, UV-Vis, UV Fluorescence, Raman, XPS, XRF, LIBS, NIR, z-nose or other analytical devices. According to one embodiment, a mobile chemical analysis device 100 includes a GC-PID module 120a and a HPLC module 120b. Various analytical device modules 120 may share sample introduction ports or analytical device modules 120 may have dedicated sample introduction ports. As such, a mobile chemical analysis device 100 may have one or more sample introduction ports.

A mobile chemical analysis device 100 can collect chemical analysis data indicating amounts of various chemical compounds in a sample, such as, but not limited to cannabinoids, terpenoids, cannabigerols, cannabichromenes, nitrogenous compounds, amino acids, and ketones. According to one embodiment, a mobile chemical analysis device 100 is adapted to analyze the composition of a cannabis based sample for classes of chemicals including, but not limited to: cannabinoids and terpenes.

More particularly, in one implementation, a mobile chemical analysis device 100 is adapted to collect the entire cannabis chemotype directly without chemical derivitization and or cannabinoid acid conversion to parent cannabinoid compound. In this context, the "cannabis chemotype" refers to both the cannabinoids and terpenoids of a sample. Embodiments may also analyze a cannabis sample for other chemical compound(s) and/or mineral content. By way of example, but not limitation the raw test data produced by the mobile chemical analysis device 100 is indicative of the presence and concentration of cannabinoids, terpenoids and other chemicals.

Mobile chemical analysis device 100 may also include integrated hardware and software to measure other compositional data. For example, a mobile chemical analysis device 100 may include integrated hardware and software to measure sample mass and moisture content.

As is understood in the art GC-PIDs and HPLC devices output voltage signals having peaks indicative of the concentration of chemicals. According to one embodiment, mobile chemical analysis device 100 may convert these signals into concentrations of chemical compounds. The conversion of the voltage signals into concentrations may occur according to any suitable method known or developed in the art. The mobile chemical analysis device 100 may store the voltage data as x,y data arrays of time versus voltage and store the chemical concentrations as a table of chemical names and concentrations. The chemicals and concentrations determined for a sample may be referred to as a "chemical signature."

In addition to raw chemical analysis data and other compositional data collected through analysis of the sample (test data), a mobile chemical analysis device 100 may collect a variety of metadata. The metadata may include environmental data. For example, each mobile chemical analysis device 100 may also include hardware and software to collect environmental data such as temperature, pressure, location information, (for example, GPS coordinates, altitude), accelerometer data and other environmental data. Other examples of metadata include but are not limited to: genotype, phenotype, cloning information, strain, location purchased, growing conditions, and growing geography.

Figure 6A:
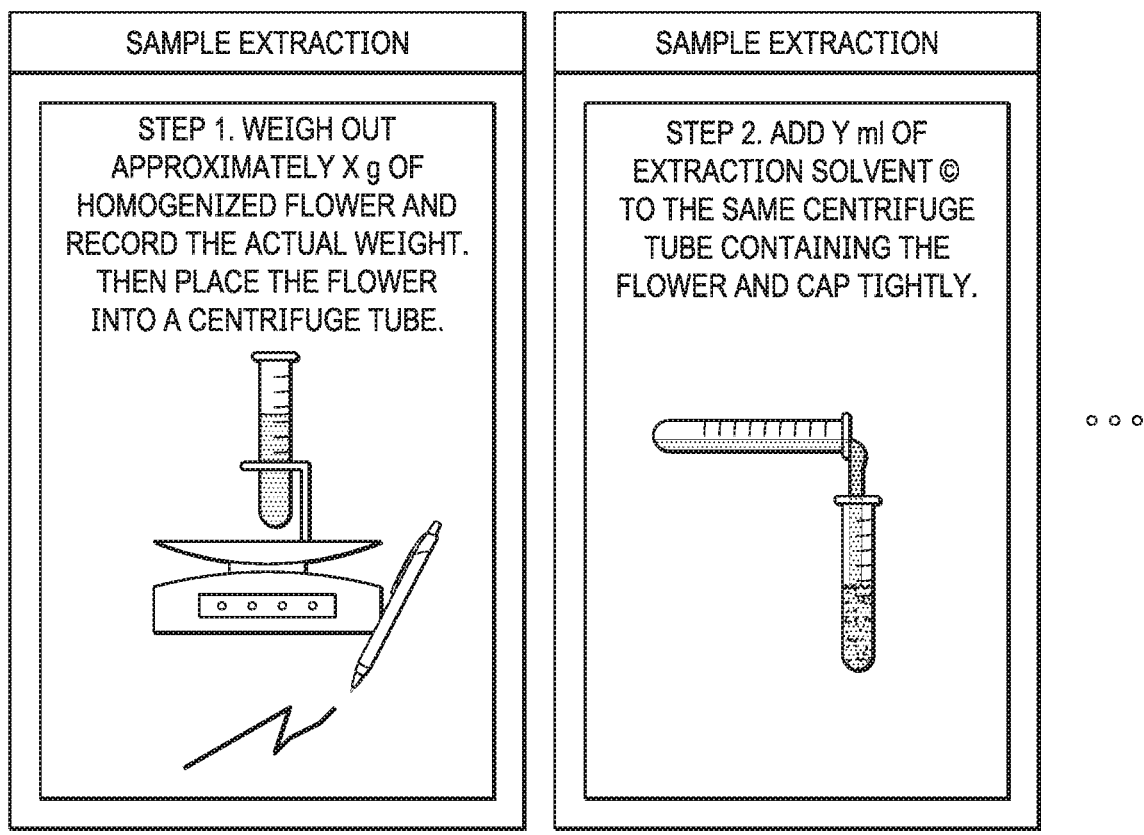
FIG. 6 (FIGS. 6A-6C) illustrate examples of user interfaces.

In one embodiment, a mobile chemical analysis device 100 provides a user interface through a touch screen, a web interface or other interface. The user interface allows a user to specify a suite of tests to perform on a cannabis sample. The sample may be assigned an internal identifier (e.g., a unique id) to differentiate it from other samples. To the extent sample preparation may be required, the user interface can provide instructions on preparing the sample or taking other actions to operate the mobile chemical analysis device (see FIG. 6A). The results of the analysis of the sample can be correlated to the sample (e.g., by unique id or other identifier). The user interface may also be configured to allow entry of a variety of metadata associated with the sample. In some embodiments, a user may also be able to enter user-provided metadata via an interface provided by chemical analysis data server 150 in addition to or lieu of providing metadata to the mobile chemical analysis device 100. According to one embodiment, a questionnaire may be presented to a user via a mobile device 152, such as tablet, laptop, or phone, connected to the Internet. The mobile device may receive the questionnaire from device 100 over the Internet, Bluetooth connection or connection and submit the response to system 100 or server 150. In another embodiment, the mobile device may receive the questionnaire from server 150 via the Internet or other channel and submit the response to the questionnaire to device 100 or 150. The interface provided through the mobile device, device 100 or server 150 can be configured to associate the response with a sample, test and/or individual user.

The test data and relevant user and non-user generated metadata may be analyzed by integrated computer system 110. However, the data is sent to chemical analysis data server 150 for more intensive processing, analysis and reporting. In one embodiment, mobile chemical analysis device 100 may send the x, y voltage data, derived concentration data, user-provided metadata and other metadata to chemical analysis data server 150 for further processing. Additional metadata may include the calibration factors and baselines used during each test in a suite of tests. The metadata may be used in the further analysis of the test data, or it may be used to control the mobile chemical analysis device. All the data related to a test or a specific user may be associated through a unique identifier.

Figure 2:
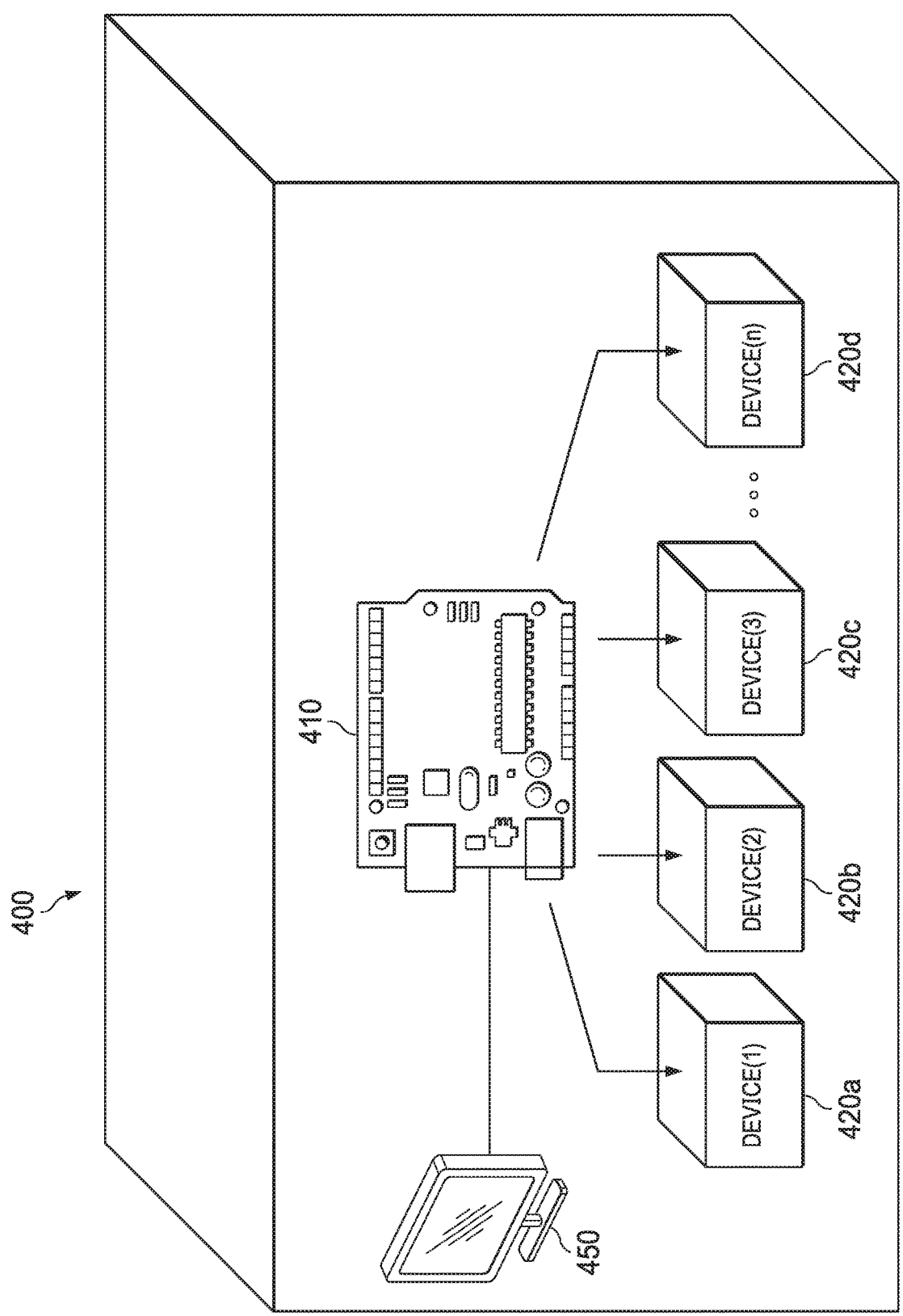
FIG. 2 is a diagrammatic representation of one embodiment of a mobile chemical analysis device.

Turning briefly to FIG. 2, FIG. 2 illustrates one embodiment of a mobile chemical analysis device 400 having a plurality of analytical device module 420. Mobile chemical analysis device 400 may be one example of a mobile chemical analysis device 100. Each module may include, for example, a controller board that plugs into or connects (e.g., via a bus) into a shared board 410. The controller board of each module may be connected to various pumps, sensors, valves, ports and other components of an analytical device module 420 to be controlled and may run module specific software (e.g., analytical device module software 220, discussed below). Shared motherboard 410 may include a processor that runs a mobile analysis device application (e.g., mobile analysis device application 210, discussed below) that coordinates analytical device modules 420, collects test, operational and status data and provides shared methods for communicating with a cloud-based platform.

According to one embodiment, mobile chemical analysis device 400 includes a touch screen interface 450 coupled to board 410. Interface screens such as illustrated in FIG. 6 may be presented to a user via interface 450. All user inputs for controlling, for example, modules 420 for running a test may be entered via interface 450.

Figure 3A:
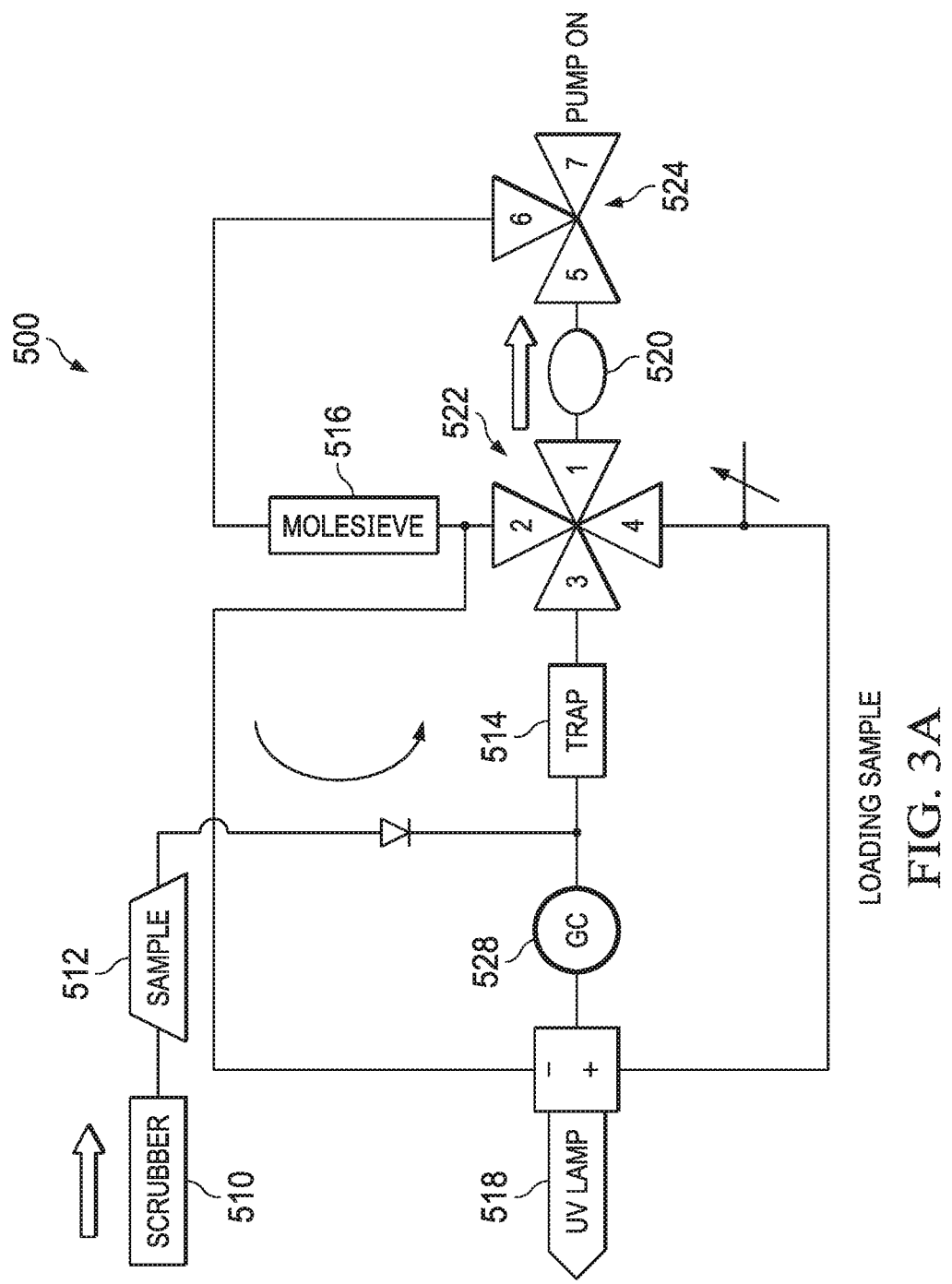
FIG. 3 (FIGS. 3A and 3B) are diagrammatic representations of one embodiment of a GC-PID module FIG. 4 (FIGS. 4A and 4B) are diagrammatic representations of one embodiment of an HPLC module.
Figure 3B:
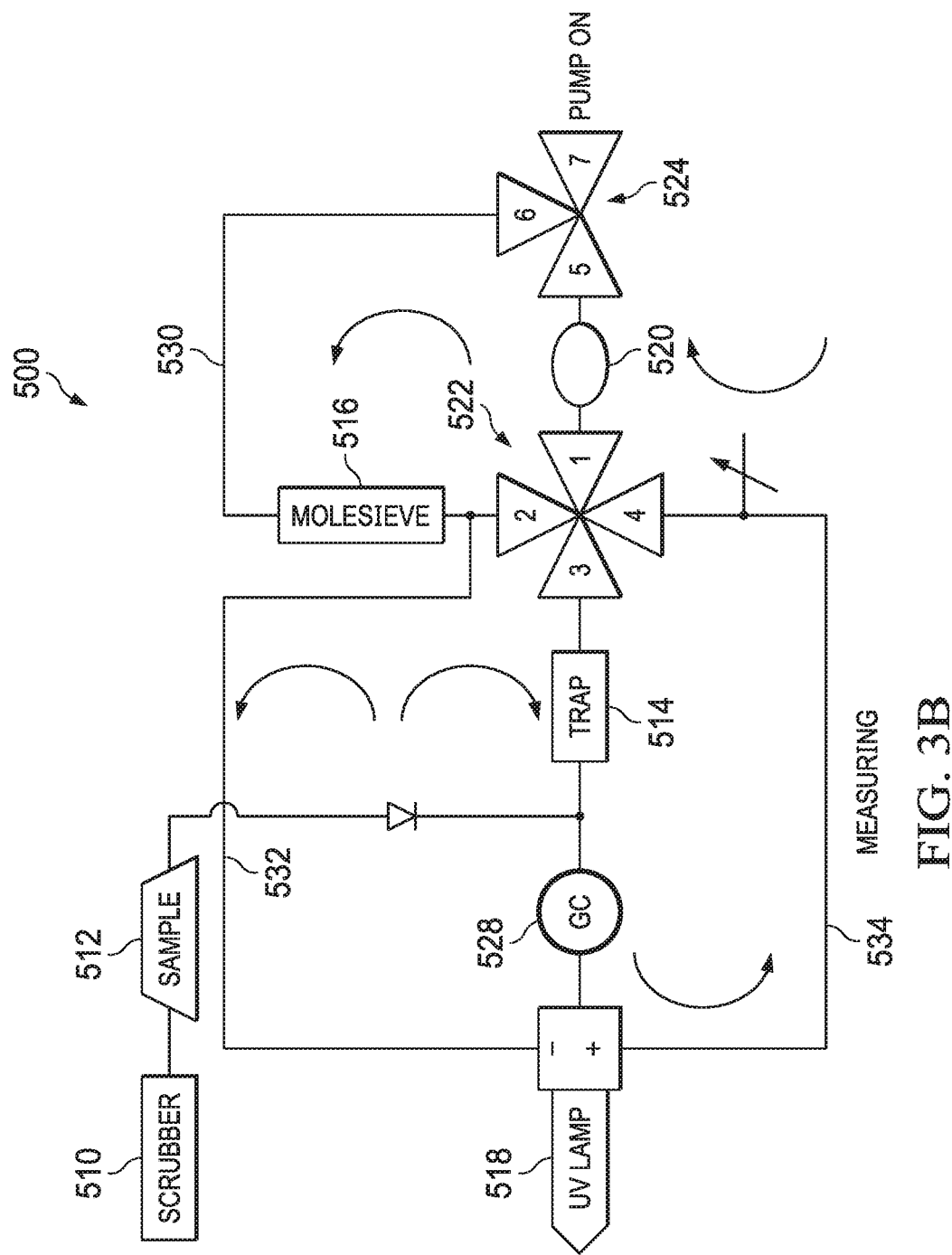

As noted above, embodiments described herein may employ various analytical device modules. The analytical device modules may have a variety of configurations. FIG. 3A and FIG. 3B illustrate a schematic diagram of one embodiment of a GC-PID module 500 comprising scrubber 510, sample injector 512, trap 514, molesieve 516, detector 518, pump 520, valve 522, valve 524, GC column 528. GC-PID module 500 may be coupled to a controller of a GC-PID analytical device module (e.g., analytical device module 120a of FIG. 1). A controller in the module (e.g., GC-PID module 120a) may control the operation of pump 520, valves 522, 524, detector 518 and other components of GC-PID module 500. GC-PID module 500 may also include a variety of sensors (temperature, pressure and other sensors) not shown. As can be noted by comparing FIG. 3A and FIG. 3B, the valves and flow passages are arranged to create a recirculation system that allows use of a single pump 520. One or more of valves 522, 524 may be a multi-way valve.

In operation, with pump 520 on, air is drawn through sample injector 512 where a sample is vaporized into various compounds that are picked up by the air as a carrier gas. The valves 522, 524 are configured in FIG. 3A so that the gas passes through trap 514 and exits GC-PID module 500. Trap 514 traps the compounds added at injector 512. In FIG. 3B, valve 524 is configured so that the gas goes through loop 530, through molesieve 516. A portion branches to loop 532 and is directed to detector 518 as makeup gas. The remainder goes back through trap 514 to pick up the trapped compounds and into GC column 528. GC column 528 separates the sample mixture into its individual components as they are swept through the column by the carrier gas, the separation being based on differential interactions between the components and an immobilized liquid or solid material within the column. Detector 518 detects and measures components as they exit the separation column. As is understood in the art, detector 518 may generate a voltage signal having peaks indicative the presence of specific compounds. Gas passing through detector 518 may return by loop 534 to pump 520.

Thus, flow can circulate back via loop 534 to pump 520. The flow moves from pump 520 to loop 530. From loop 530 the flow then splits to loop 532 and trap 514. In this way, the gas is recirculated and no external ambient gas or moisture gets in. This provides the benefit that the lifetime of molesieve/dry condition can be very long, for example, a year compared to hours or days. Furthermore, the embodiment of FIG. 3 eliminates the need of pure gas from gas cylinder and prolongs the lifetime with minimum service and consumable items.

The controller of GC-PID module 500 may pass the voltage signal or a processed voltage signal to, for example, mobile analysis device application 210. GC-PID module 500 may also pass operational data such as sensor readings, timings and other data. The voltage signal may be transformed by, for example, analytical device module software 220a (discussed below) or mobile analysis device application 210, into measurements of concentrations of various compounds. In one embodiment, the voltage signal is transformed at the mobile chemical analysis device 100, 400 into the concentration of each of a plurality of terpenoids and/or residual solvents. In some embodiments, the raw test data provided to chemical analysis data server 150 will include an x,y data array of time versus voltage and metadata including the user-provided metadata, a table of compounds with related concentrations and other data.

Figure 4B:
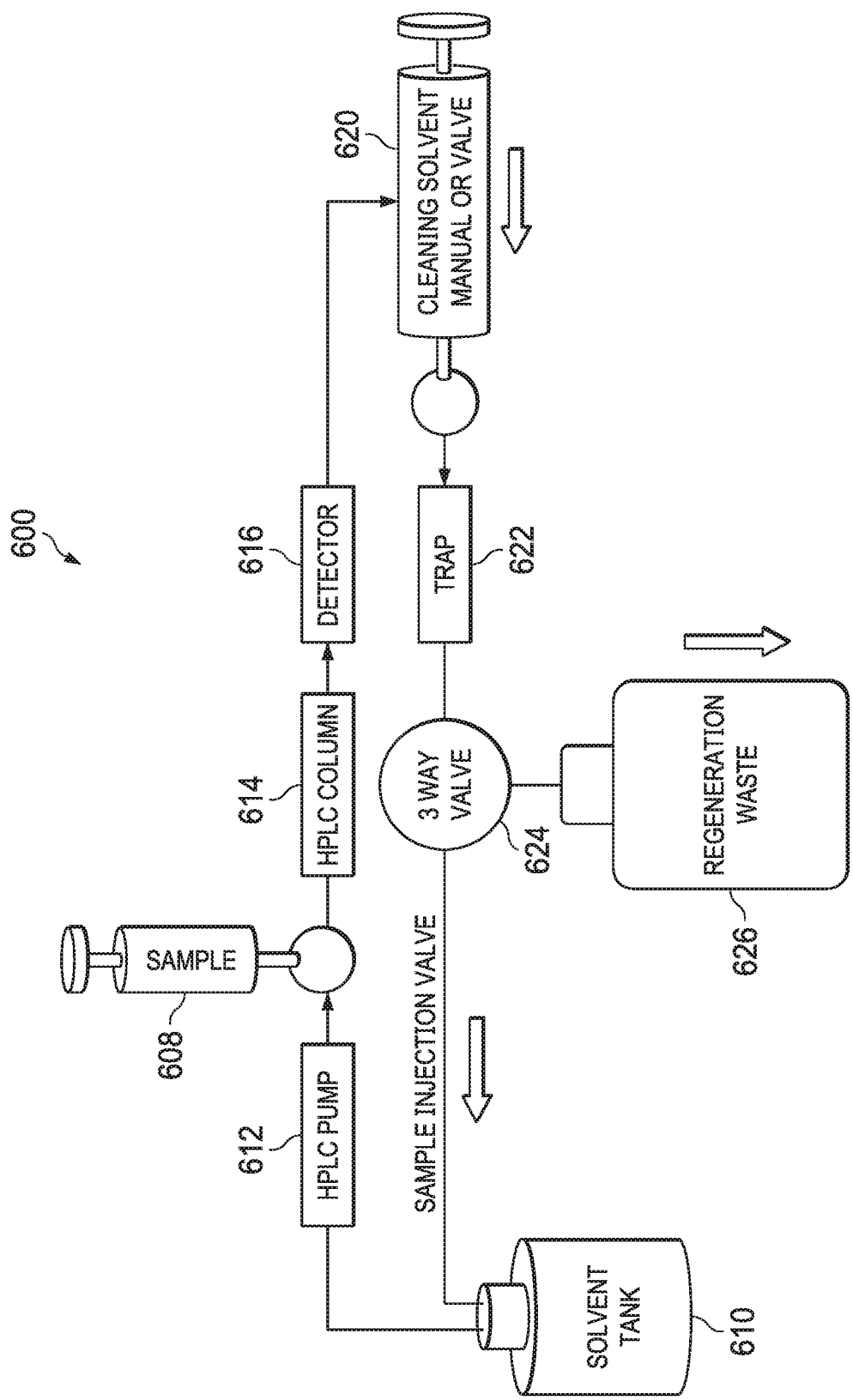

FIG. 4A and FIG. 4B are diagrammatic representation of one embodiment of an HPLC module 600. HPLC module 600 comprises a solvent tank 610, HPLC pump 612, sample injector 608, HPLC column 614, detector 616, valve 620, trap 622, valve 624, regeneration waste 626 and cleaning solvent injector 628. While only a single HPLC column 614 is illustrated, HPLC module 600 may include any number of HPLC columns 614. HPLC columns 614 can be arranged in series or parallel. A controller in the module (e.g., HPLC module 120b) may control the operation of pump 612, injector 608, valves 620, 624, injector 628, detector 616 and other components of HPLC module 600. HPLC module 600 may also include a variety of sensors (temperature, pressure, solvent tank volume, regeneration waste tank volume, and other sensors) not shown. In some embodiments, a valve may be provided such that the user can select which HPLC column 614 to use when multiple parallel columns of different types are provided.

As illustrated in FIG. 4A, pump 612 draws solvent from solvent tank 610 and pushes the solvent through sample injector 608, HPLC column 614, and detector 616. Valve 620 and valve 624 are configured so that the solvent passes through trap 622 and returns to solvent tank 610. Trap 622 removes the compounds injected at injector 608.

As illustrated in FIG. 4B, when trap 622 is to be regenerated, valves 620 and 624 are configured to isolate the trap 622. Cleaning solvent may be injected manually, through an injection valve or other mechanism. Valves 620 and 624 are configured to allow the cleaning solvent to flow through trap 622 and to regeneration waste tank 626. Regeneration waste tank 626 may be periodically emptied.

The controller of HPLC module 600 may pass the voltage signal or a processed voltage signal to, for example, mobile analysis device application 210. HPLC module 600 may also pass operational data such as sensor readings, timings and other data. The voltage signal may be transformed into measurements of compounds by, for example, analytical device module software 220a (discussed below) or mobile analysis device application 210 (discussed below). In one embodiment, the voltage signal is transformed at the mobile chemical analysis device 100, 400 into the concentration of each of a plurality of cannabinoids and/or terpenes. In some embodiments, the raw test data provided to chemical analysis data server 150 will include an x,y data array of time versus voltage and metadata including the user-provided metadata, a table of compounds and corresponding concentrations and other data.

It can be noted that the example modules provided in FIGS. 3A, 3B, 4A and 4B are provided by way of example and not limitation. Embodiments described herein may utilize any suitable modules.

Returning to FIG. 1, embodiments described above can provide a system that promotes data integrity and reliability. Embodiments can ensure accurate results when tests are run on the same device or across devices. For example, all devices 100 may be created and tested in highly controlled conditions to minimize tool the tool variation. In addition, each mobile analysis device 100 perform internal calibration and system health checking during every run. In one embodiment, a mobile analysis device 100 may include calibrant installed inside the device 100 (for example, in small gas cylinder, via permeation tube or compartment). The calibrant is injected into the appropriate module 120 by I/O control, typically at each run. From the detected calibrant signal, mobile device 100 or server 150 can make a determination, based on rules, of whether the system 100 is in good order, or determine if parameters require adjustment.

The results of a internal calibration or other health checking may trigger an external calibration. With external calibration, calibrant is provided from a source outside of the device 100. A user can change the calibrant source easily. External calibration may be triggered according to a prefixed time frequency, or preset logic by user's command. Integrated computer system 110 or individual modules 120 may store appropriate calibration data (e.g., calibration curve coefficients or other calibration parameters) determined from internal or external calibration.

Calibration data for a module 120 may be developed by analyzing the response of the module to samples of "known" concentration. For example, vials of various concentrations can be used to build calibration data for the HPLC, GC-PID or other module; however, the concentrations of the standard kits may be controlled by the entity manufacturing or providing systems 100 and are unknown to the technician 175 performing calibration. A mobile analysis device 100 can pass responses to standard kit testing to data server 150 (e.g., with a standard kit id identifying the sample tested) and data server 150 can generate the calibration data for a module 120 using the known concentrations stored at data server 150. In another embodiment, data server 150 may pass the known concentrations for standard kits to device 100 and the device 100 can develop the calibration data. In any case, the known concentrations of the standard kits may be stored and communicated in a manner such that they are not accessible by the end user of the device 100 and, in some cases, are only accessible by users with sufficient credentials, such as users associated with the manufacturer. Because the concentrations are unknown to the end user running a calibration, the user cannot successfully game the sample by altering the concentration. Moreover, the chemical mixtures in the calibration kits can change from time to time to further ensure integrity.

Calibration may be automatically triggered based on one or more rules such as, but not limited to:

a. scheduled calibration requirement after certain run numbers;
b. calibration required after a certain number of days without calibration;
c. baseline drift;
d. total chemical contents below certain threshold;
e. device has not be running for certain time.

The calibration parameters for a mobile analysis device 100 may be encrypted or encoded so that a record of calibration parameters used cannot be altered.

To further promote integrity and reliability, an entity providing mobile chemical analysis device 100 (e.g., the manufacturer) or providing certification of devices can occasionally send blind samples that are unknown to the users of mobile chemical analysis device 100. The results of testing the unknown samples can be automatically compared to the blind sample's known results. This can be used to identify the best mobile chemical analysis device 100 and match other tools to the best tool. For example, the calibration parameters, baselines and/or other device configuration data from the best tool can be pushed out to the other tools because the calibration factors and baselines may be stored, for example, in the cloud.

According to one embodiment, a mobile analysis device 100 may be adjusted for environmental changes. For example, operating parameters of a mobile analysis device 100 may be changed to alter pump speed due to geographic elevation pressure change to ensure the consistent GC flow rate. As another example, system calibration parameters may be temperature, pressure or other environmental factor dependent.

To further promote data integrity and reliability, the user end software is simple so user interaction is identical or otherwise designed to minimize user induced variation. In addition, data output can be provided in non-editable formats.

Chemical analysis data server 150 may comprise one or more computer systems with central processing units executing instructions embodied on one or more computer readable media where the instructions are configured to perform at least some of the functionality associated with embodiments of the present invention. According to one embodiment, chemical analysis data server 150 provides a cloud-based chemical analysis data system. These applications may include one or more applications (instructions embodied on a computer readable media) configured to provide customer relationship management (CRM), test tracking and billing, device performance tracking and monitoring, on-line troubleshooting, chemical library, analytical software updates and advanced analytics including, but not limited to: pre-processing, filtering, supervised and unsupervised learning, support vector machine learning, PCA, PLS-DA, clustering, classification, association, Bayesian networks, deep learning, and other analytic approaches.

Chemical analysis data server 150 may provide an enterprise cloud-based system that supports multiple accounts or tenants. Access to certain data may be segregated based on account. Furthermore, the ability to perform tests using mobile chemical analysis device 100 may be tied to an account. For example, an entity using a mobile chemical analysis device 100 may have to have a particular account type or account status to run tests using the mobile chemical analysis device 100. Chemical analysis data server 150, however, may collect data from mobile chemical analysis devices 100 controlled by multiple account holders.

The accuracy and precision of the devices is of paramount importance in some embodiments, as a user may purchase or sell a product based on an analysis generated by one of the mobile chemical analysis devices. Consequently, some embodiments may track and log device results and metadata associated with the test and/or the device. The tracking and logging of this data may be performed with respect to all devices, or it may be triggered by a determination that the results generated by a particular device were not accurate.

In order to ensure that device performance is not the cause of inaccurate or imprecise results, advanced methods of multivariate fault detection (MVFD) are employed in some embodiments. Individual mobile chemical analysis devices monitor various system parameters such as temperatures, pressures, voltages, flow rates, retention times, areas, etc. The devices may also monitor temporal behaviors, including tracking variables over time. Still further, the devices may track events associated with the respective devices (e.g., if a user drops a device, this may be detected via an accelerometer, and the event information may be logged). The tracked data can be introduced into the models of the chemical analysis data system (e.g., preprocessing, filtering, supervised and unsupervised learning, support vector machine learning, PCA, PLSDA, clustering, classification, association, Bayesian networks, deep learning, and other analytic models).

Based on the tracked device data received from the individual mobile chemical analysis devices, the system can determine whether the devices are operating within their expected WECO rules (Western Electric rules—see https://en.wikipedia.org/wiki/Western_Electric_rules) as well as within their multivariate control space. Additionally, this same data can be used to perform "fleet matching" of the mobile chemical analysis devices. That is, the chemical analysis data system can analyze the collective data of the mobile chemical analysis devices in order to determine whether any of the individual devices are operating in a manner that deviates by some statistically significant amount from the rest of the devices.

In one embodiment, the chemical analysis data system uses multivariate analysis of the device data collected from the individual mobile chemical analysis devices to detect faults (deviations from expected parameters that are derived from the data for the larger group of devices). In this way, the system ensures that all of the devices in the "fleet" match, or operate to produce consistent, accurate results. This analysis may be performed by a machine learning system that can be trained, initially with previously collected data, as well as with current data that is provided by the devices. Training data for the multivariate models can be collected in stages, starting with lab devices, then demonstration devices, then pilot devices, then actual deployed fleet devices. When a fault is detected in one of the devices, the system may take a variety of actions. These actions may range from providing a warning flag (notifying a local user of the device that a recalibration is necessary) to remotely adjusting operating parameters of the device, shutting down the device, or if the device is being tampered with, even having the device self-destruct in a non-dangerous manner (e.g., a dead man switch).

In operation, a client user 170 seeking to have a sample tested can bring a sample a technician 175 operating a mobile analysis device 100 to test a cannabis sample. Using a user interface, such a user interface provided on a display device of mobile chemical analysis device 100, a web app or other interface, the technician may indicate that a test of a sample of is to be performed (a sample test). The technician 175 may have to perform a biometric scan or credentials verification before the sample test can be run by the technician.

Mobile chemical analysis device 100 and chemical analysis data server 150 may cooperate to determine if a test can be run. For example, mobile chemical analysis device 100 may communicate to chemical analysis data server 150 that a test is to be performed and chemical analysis data server 150 can check device management data for the mobile chemical analysis device 100 and apply a set of device management rules to approve or prevent the test from occurring.

Example rules that may prevent a test from running include, but are not limited to:
- a. failing a calibration or not doing a required calibration; e.g., require calibration if x or more days since last calibration.
  - require calibration if y tests run since the last calibration
- b. require calibration if baseline shift of X % occurs detecting baseline shifts in detector performance;
  1. require calibration if baseline shift of greater than z % or other threshold amount occurs
  - detecting baseline shifts in elution times or peak widths;
    1. require calibration if baseline shift of greater than z % or other threshold amount occurs
  - baseline shifts in pressure, flow, temperature zones, heating and cooling cycles;
    1. require calibration if baseline shift of greater than z % or other threshold amount occurs
- c. detecting the appearance of new/unknown peaks;
- d. unexpected co-elution of peaks;
- e. device is dropped or mishandled and accelerometer alarms;
- f. non-payment of fees;
- g. violating use agreement;
- h. leaving geo-fence area;
- i. tampering with the device.

When it is verified that a test can be run, a unique Test ID (TID) is assigned. The TID may be generated based on a combination of parameters such as data, time, GPS coordinates, unique technician ID or other parameters.

The mobile chemical analysis device 100 also assigns a Unique Intake Identification Number (UIIN) that follows the sample. In some embodiments, the UIIN may be a QR code. Various methods may be implemented to ensure each sample is assigned a unique UIIN within a system. For example, chemical analysis data server 150 may track UIINs and mobile chemical analysis device 100 may communicate with chemical analysis data server 150 to receive a UIIN when a new sample is to be tested. A UIIN+TID combined file is assigned in a database at mobile chemical analysis device 100 for intake of data.

The mobile chemical analysis device 100 may provide, via a user interface, a questionnaire to enter user-provided metadata, which may depend on the type of client user, such as whether the client user 170 is a grower or a purchaser. The questionnaire can be administered via a mobile device (phone, tablet or other device). The collected information may include, by way of example, but not limitation:
1. Client contact information (These can be automated by an assigned customer number after an initial test);
2. Product Type; Flower, Concentrate, Edible, Topical, Other;
3. Geographic Region—Zip code;
4. Strain Name
5. Strain Type
6. Grower/Growing Style (type) e.g., Outdoor, Indoor
   - Extraction Method (type) for concentrates—supercritical $CO_2$, ethanol, or other method;
   - Specialty Grow Technology (type)—hydroponic, aquaponic, aeroponic, or other method;
   - Nutrient(s) and Fertilizers;
   - Lighting; (Drop down) Natural, SH, LED, or other.
7. Patient Questionnaire (illnesses, symptoms, desired effect, actual effects, frequency of use).

The questionnaire may be provided to the technician 175 and the technician may provide the questionnaire to the user 170 with a sample to be tested. In some cases, the technician 175 may enter metadata for the user. In another embodiment, the client user 170 may interface with the mobile analysis device 100 or chemical analysis data server 150 to provide at least a portion user-provided metadata. For example, client user 170 may use a web application to provide user-produced metadata such as patient questionnaire data. The user-provided and other metadata is attached to the intake data file. In addition, other metadata such as environmental data, identity of the mobile chemical analysis device 100 and any other metadata may be attached to the intake data file.

According to one embodiment, the user interface presented to technician 175 allows the technician to capture a digital image of the sample using a camera on the mobile chemical analysis device 100, the technician's mobile device (e.g., smart phone) or other device. The sample digital image is attached to the unique intake data file for the test.

The technician 175 selects cannabinoid test or terpene test or both cannabinoid and terpene tests to be run as part of the sample test and performs any necessary sample prep procedures, which may be dependent on the types of analytical device modules 120 used and the suite of tests performed. The selection of tests establishes a control flow for collecting data from analytical device module 120 so that data is correlated with test (e.g., with UIIN+TID).

The technician may also select a destination for a report, such as a .pdf report sent to a selected destination or a report sent to a pre-set online display or laboratory information management system output.

As the analytical device modules 120 process the sample, integrated computer system 110 can gather collected test data in the intake data file. When the test is completed, integrated computer system 110 can send the intake data file to chemical analysis data server 150. In another embodiment, integrated computer system 110 may send collected metadata and test data to chemical analysis data server 150 (e.g., to the cloud) as the data is collected by integrated computer system 110. In yet another embodiment, analytical device module 120 may send data directly to chemical analysis data server 150 (e.g., if the module 120 includes a network interface device).

Reports may be provided in a format in which there is no ability to edit results. Furthermore, chemical analysis data server 150 may prevent any editing of result data at chemical analysis data server 150.

Chemical analysis data server 150 can aggregate a large amount of data from a plurality of mobile chemical analysis devices 100 and provide real time data analysis on big data sets. Chemical analysis data server 150 provides rich metadata collection and data redundancy. Chemical analysis data server 150 can store a library of chemicals in the cloud and push new chemicals in the library to devices 100 automatically to allow devices 100 to identify the new chemicals.

Further, chemical analysis data server 150 allows user-based R&D (allow super users to run chemicals that are not in library).

Chemical analysis data server 150 may collect data from a large number of users, samples and mobile chemical analysis devices 100. Through machine learning based on the test data and metadata, chemical analysis data server 150 can perform various analysis, such as, but not limited to:

Matching users to desired and/or undesired chemotype(s) that they have previously identified or that others like them have identified.

Determining relationships between phenotype (grow) impact on chemotype. For example, the same genotype may result in different chemotypes depending on phenotype. Such information may be used to increase the reliability of production process. For example, the phenotype information for a desired chemotype can be used to control irrigation and other environmental conditions to create the proper grow.

Providing standardization of strains. For example, determining a chemotype (chemotype cluster) for a strain based on a large number of samples and determining if a tested sample that purports be that strain matches the chemotype for that strain.

Matching chemotype to possible genotype(s) and phenotype(s).

Matching chemical signature to previous chemical signatures for process control, QC/QA.

Identifying potentially new chemotypes.

Thus, system 10 can provide compliance tracking. Furthermore, chemical analysis data server 150 may promote standardization of strains.

Figure 5:
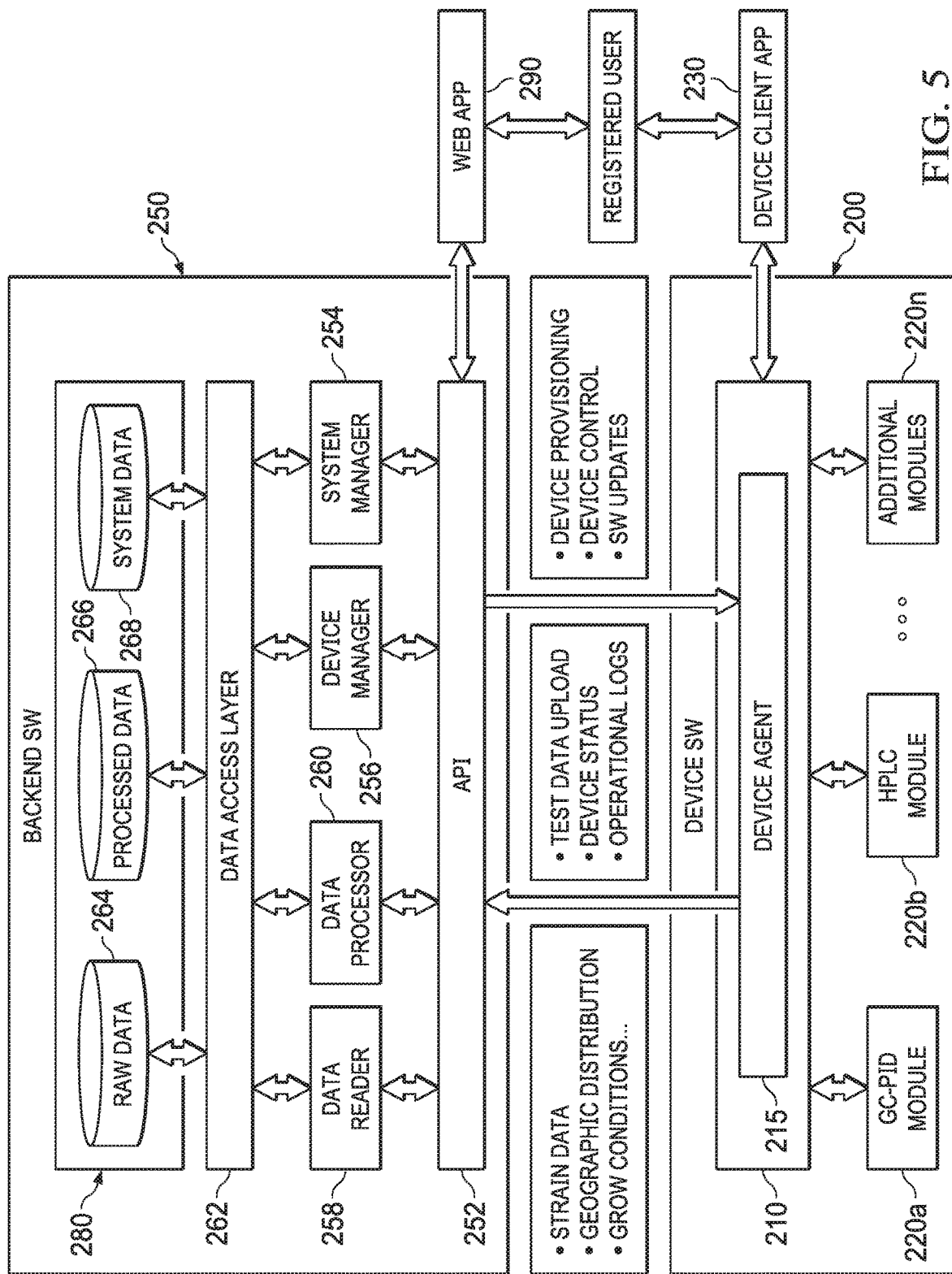
FIG. 5 is a diagrammatic representation of one embodiment of a software architecture for an embodiment of a chemical data analysis system.

FIG. 5 is a diagrammatic representation of one embodiment of software architecture of chemical data analysis system. FIG. 5 includes a mobile analysis device 200 connected to a remote chemical analysis data system application 250. Mobile analysis device 200 may be an example of mobile chemical analysis device 100, 400 and chemical analysis data system 250 may be an example of chemical analysis data server 150.

Mobile analysis device 200 includes a mobile analysis device application 210 configured to manage sample tests, collect user-provided metadata and other metadata, collect test data and related metadata, collect operational logs, collect status information and perform other tasks. Mobile analysis device application 210 may include a mobile analysis device agent 215 that communicates with chemical analysis data system 250 to communicate a variety of data to chemical analysis data system 250 including operational logs and device status data. Metadata, such as user-provided metadata and other metadata associated with a sample test, test data, device status data and operational logs. As discussed above, test data and related metadata may be associated with a UIIN and TID (or other unique identifier).

The operational logs may include a variety of information collected by mobile analysis device application 210 including data provided by analytical device module software 220 (e.g., date, time, pressures, temperatures, cycle data collected during a test) and other data. In some embodiments, operational log information may be associated with test data. Operational log data may also include data such as accelerometer alarms, product tampering alarms or other operational information. Device status data can include various types of environmental information, whether the device is online, whether the device is running, whether a particular analytical device module is installed or available, the location of the device and other status information.

Mobile analysis device application 210 communicates with analytical device module software 220 to initiate tests, receive test data and perform management tasks (e.g., provide calibration data, receive calibration results, update analytical device module software 220 and perform other operations). The respective analytical device module software 220 can be responsible for controlling the pumps, valves, motors and other components of the respective module (e.g., analytical device module 120) to perform an analysis and return analysis results to mobile analysis device application 210.

Mobile analysis device application 210 may provide an interface for one or more mobile analysis device client applications 230. The applications may allow a user (e.g., a technician) to initialize a sample test and provide user-provided metadata. The user supplied metadata can be provided via a mobile device connected to system 200 or 250 via the Internet or other communication channel. The interface utilized in a given context may depend on the functionality being implemented by mobile analysis device 200, the type of network utilized to communicate with any particular entity, the type of data to be obtained or presented, the time interval at which data is obtained, the types of systems utilized at the various entities, etc. Thus, these interfaces may include, for example web pages, web services, a data entry or database application to which data can be entered or otherwise accessed by an operator, APIs, libraries or other type of interface which it is desired to utilize in a particular context.

Chemical analysis data system 250 may provide a wide degree of functionality including utilizing one or more interfaces 252 configured to, for example, receive and respond to queries from users at client computing devices, receive and respond to queries from mobile analysis devices 200 and configure or manage mobile analysis devices 200. The interface 252 utilized in a given context may depend on the functionality being implemented by chemical analysis data system 250, the type of network utilized to communicate with any particular entity, the type of data to be obtained or presented, the time interval at which data is obtained, the types of systems utilized at the various entities, etc. Thus, these interfaces may include, for example web pages, web services, a data entry or database application to which data can be entered or otherwise accessed by an operator, APIs, libraries or other type of interface which it is desired to utilize in a particular context.

In the embodiment illustrated, chemical analysis data system 250 further includes system manager 254, device manager 256, data processor 260, data reader 258 and data access layer 262. Chemical analysis data system 250 stores a variety of data in one or more data stores including raw data 264, processed data 266 and system data 268. Data access layer 262 can provide services for other components to store data in data store 280. Data reader 258 provides services to read data from data store 280 via interfaces 252.

Raw data comprises data collected from one or more mobile analysis devices 200. Raw data 264 from one or more mobile analysis devices 200 may be stored in a data lake that stores data in its native format. The data lake facilitates the collocation of data in various schemata and structural forms, including for example, as object blobs or files. The data lake may include unstructured data, structured data from disparate relational databases, semi-structured data and other forms of data. Raw data may include, for example, test data and related metadata received from mobile analysis devices 200. The raw test data and associated metadata may be organized based on UIIN+TID.

Operational logs and device status data may be organized based on a unique id for a mobile analysis device 200.

Data processor 260 may process raw data 264 to generate processed data 266 and process processed data 266 to generate further processed data 266. Processed data 266 includes data determined during operation, and rules/models (such as machine learning models) that may be applied to raw data 264 or processed data 266 to generate further processed data 266 and which may comprise, for example, models or rules for data processor 260 to match users to desired chemotype(s) that they have previously identified or that others like them have identified, determine relationships between phenotype (grow) impact on chemotype, determine if a chemical signature matches a strain, match chemotype to possible genotype(s) and chemotype(s), match chemical signature to previous chemical signatures for process control and/or QC/QA.

System manager 254 can be responsible for administrative functions, such as account management and general configuration and management of the system. System information 268 can include system configuration information, account information and other information used to administer and configure the system of FIG. 5.

Device manager 256 can provide services to provision mobile analysis devices 200, track software versions on mobile analysis devices 200, provide software updates to mobile analysis device 200 and provide device control data such as calibration curves and other device control data to devices 200.

Device manager 256 may analyze operational logs and status information from a mobile analysis device 200 and prevent the mobile analysis device 200 from performing further tests if it detects that the mobile analysis device 200 is not in a 'ready' state (i.e. failed a calibration, did not perform a required calibration or other error state detected). Furthermore, device manager 256 can analyze test data and operational logs provided by a mobile analysis device 200 to determine if, over time, there has been a baseline shift in detector performance, elution times, peak widths, pressure, flow, temperature zones, heating and cooling cycles. Device manager 256 may also determine from operational logs or status data if the mobile analysis device 200 has been dropped or mishandled based on accelerometer alarms or other alarms or if the mobile device 200 has moved out of an allowed geo-fenced area. Device manager 256 may analyze system data 268 to determine if an account associated with mobile analysis device 200 is paid up, or if there are any violations of user agreements. Device manager 256 may apply device management rules to prevent a test from occurring.

In operation, a mobile analysis device 200 may be provisioned by cannabis analysis data system 250. Device provisioning includes the initialization of the mobile device, such as enabling GPS location, network configuration, data routing path preparation, device/user authorization (encrypted hand-shake), challenge, verification, push notifications, etc. Device provisioning may include the process of attaching a certificate to a device identity. Device identity (or in short—device ID) is used to uniquely identify a specific device. Device identity can be used for various features, such as push notifications and reporting. The device ID may be automatically generated by the client-side framework when requested by the chemical analysis data system 250. The device ID is used to uniquely identify a specific device 200 with the chemical analysis data system 250. According to one embodiment, mobile analysis device provisioning may include provisioning according to the IBM MOBILEFIRST PLATFORM FOUNDATION.

At provisioning and throughout the life of the mobile analysis device 200, chemical analysis data system 250 can send calibration data (e.g., calibration curves or other calibration data) software updates and other data to mobile analysis device 200. As mobile analysis device 200 operates, it sends operational logs and device status data to chemical analysis data system 250.

With reference to FIG. 5, FIGS. 6A-6C, a user using mobile analysis device client application 230 can indicate that a sample test is to be run. The user may have to perform a biometric scan or credentials verification before the sample test can be run. Mobile analysis device agent 215 can send the test request to device manager 256 and device manager 256 can apply device management rules to determine if the test can be run. Device manager 256 can send device control data to mobile analysis device 200 indicating which tests can be run and/or steps needed to perform the tests. For example, device manager 256 may prevent a test from being run if one or more analytical device modules have to be calibrated before a test can be run based on, for instance, days since last calibration, tests run since last calibration, baseline shifts and/or other rules as discussed above. In one example, the GC-PID module may have to be calibrated. The user may be given the option to calibrate one or more of the analytical device modules.

In some cases, the calibrations are automated. The user simply selects to perform the calibration and mobile analysis device application 210 and analytical device module software 220 cooperate to perform the calibration. In some cases, mobile analysis device application 210 may fetch updated calibration curves from device manager 256 and provide the calibration curves (or other calibration data) to the analytical device module software 220 for the module. In another embodiment, calibration may include performing a calibration using standard kits as discussed above to develop updated calibration data. In some cases, if the standard kits are already installed or if the updated calibration data is already stored at 250 (e.g., based on a best machine), the system requires no further user interaction to complete the calibration of the GC-PID. In other embodiments, the user may have to insert calibration samples using a standards kit to perform calibration runs.

As discussed above, device manager 256 may prevent the test from proceeding for a variety of other reasons based on past test data from the mobile analysis device 200, operational logs or device status information. For example, device manager 256 may send device control data to mobile analysis device 200 indicating that a test cannot proceed based on device error states, detected baseline drifts, possible device damage (e.g., accelerometer alarms), overdue accounts and other rules-based reasons.

Figure 6B:
Figure 6C:
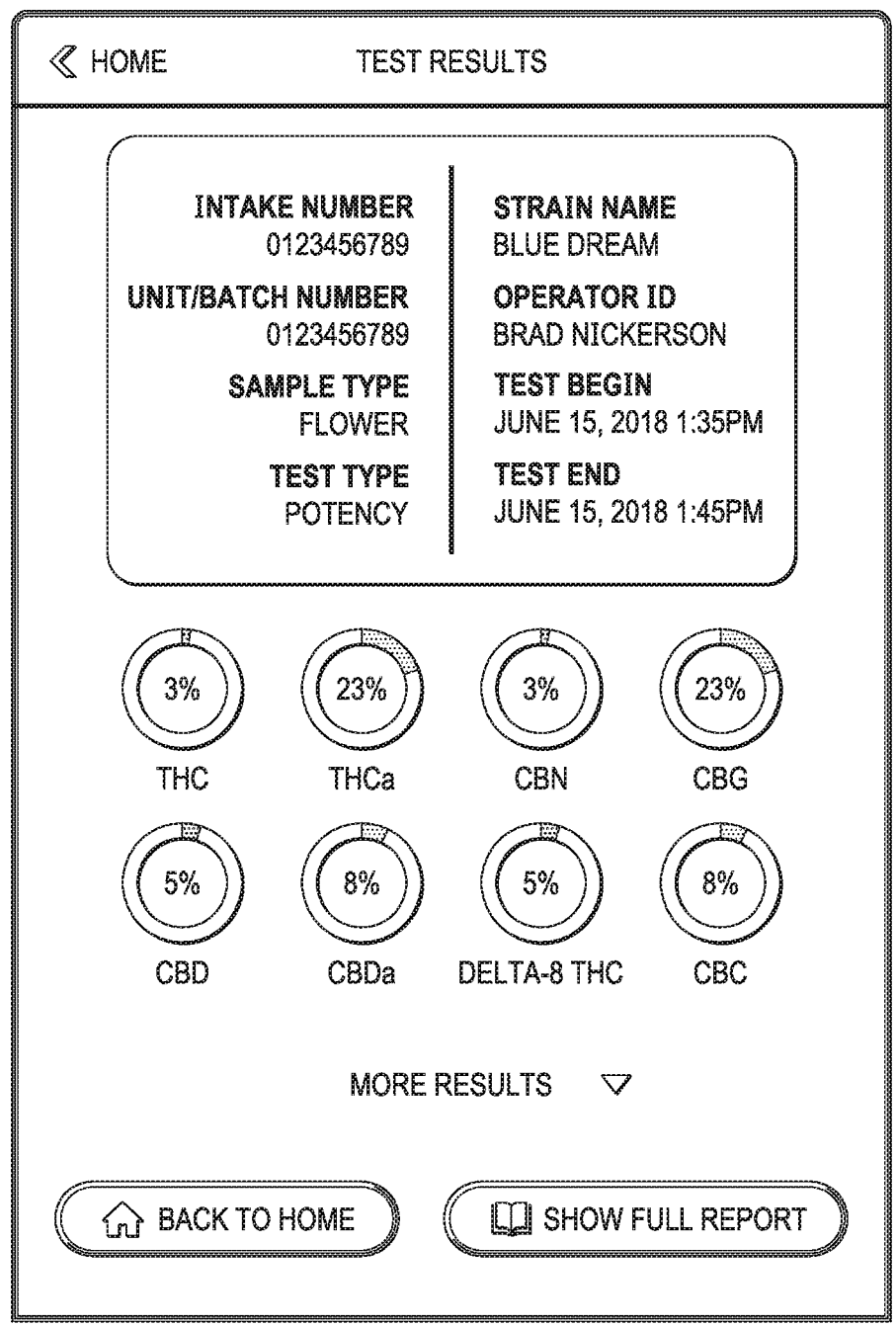

When it is verified that a test can be run, mobile analysis device application 210 assigns a Unique Intake Identification Number (UIIN) that follows the sample (illustrated as Intake Number in FIG. 6B). In some embodiments, the UIIN may be a QR code. Mobile analysis device application 210 also assigns a unique Test ID (TID). The TID may be generated based on a combination of parameters such as data, time, GPS coordinates, unique technician ID or other parameters.

Various methods may be implemented to ensure each sample is assigned a unique UIIN within a system. For example, chemical analysis data system 250 may track UIINs and mobile chemical analysis device 200 may communicate with chemical analysis data system 250 to receive a UIIN when a new sample is to be tested. A UIIN+TID combined file is assigned in a database at mobile chemical analysis device 200 for intake of data.

Mobile analysis device application 210 may provide, via a user interface, a questionnaire in mobile analysis device client application 230 on an Internet connected device. As discussed above, the questionnaire may ask a variety of questions to collect user-provided metadata. Further, as illustrated in FIG. 6B, the user interface provided in mobile analysis device client application 230 allows the user to capture a digital image of the sample using a camera on the user's mobile device (e.g., smart phone) or other device. Mobile analysis device application 210 attaches the image to the unique intake data file for the test.

The user selects the suite of tests to be run as part of the sample test and performs any necessary sample prep procedures, which may be dependent on the types of analytical device modules used and the suite of tests performed. In some embodiments, the user may be given the option of running some or all of the tests in parallel or ordering the tests in series.

The user may select to run all the available tests or some subset thereof, such as a single test. The user may also select a destination for a report, such as a .pdf report sent to a selected destination or a report sent to a pre-set online display or laboratory information management system output.

As the analytical device modules process the sample, mobile analysis device application 210 can gather collected test data in the intake data file. For example, mobile analysis device application 210 can receive indications of terpenoids and residual solvents from GC-PID module software 220*a* and indications of cannabinoids from HPLC module software 220*b*. Mobile analysis device application 210 may perform some processing of the test data. When the test is completed, mobile analysis device agent 215 can send the intake data file, which may include data processed by mobile analysis device application 210, to chemical analysis data system 250 for storage as raw data 264. Mobile analysis device application 210 may also output the test results to mobile analysis device client application 230 (see, e.g., FIG. 6C).

Processing module 266 may process the test data and generate a more detailed report. For example, process module 266 may certify that, based on the chemotype, the sample is the strain that it is purported to be in the user-provided metadata. It can be noted that the test results and processed data can be output in formats that cannot be edited.

Chemical analysis data system 250 may further allow searching of sample and test data, and may provide other services.

Figure 7:
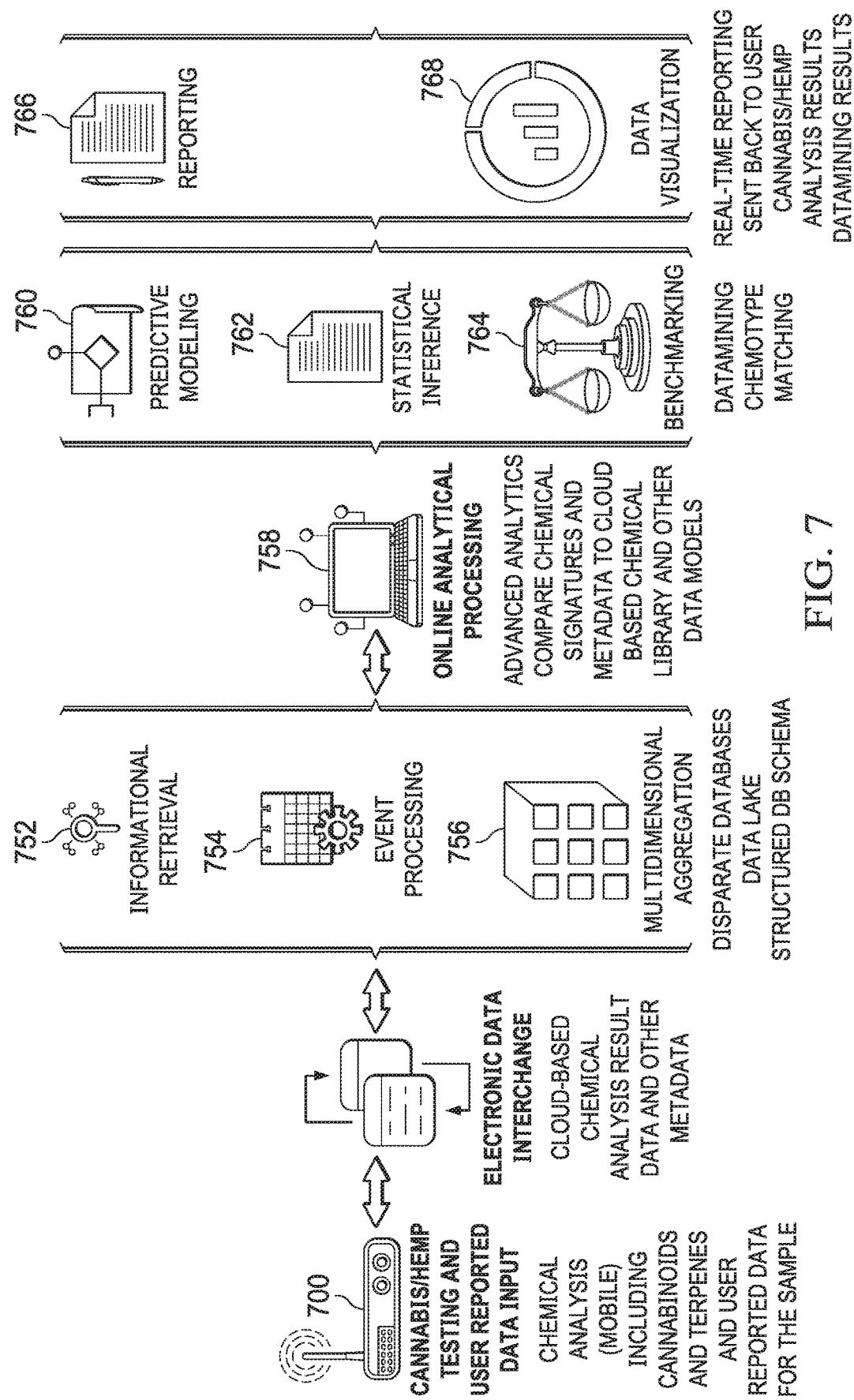
FIG. 7 is a diagrammatic representation of one embodiment of a chemical data analysis system.

FIG. 7 illustrates one embodiment of a cannabis data analysis system 699 comprising a mobile chemical analysis device 700, which may be one example of mobile chemical analysis device 100, 200, 400, coupled to a cloud-based chemical analysis data system 750, which may be one embodiment of a chemical analysis data server 150, 250. FIG. 7 illustrates various functional blocks.

When mobile chemical analysis device 700 indicates a request to conduct a sample test, event processing 754 can initiate process to manage the event. For example, information retrieval 752 may pulls information from mobile chemical analysis device 700 and information from chemical analysis data system 750. Information retrieval 752 can use this information to determine whether the calibrations are up to date and the baselines are appropriate. Information retrieval 752 may also check for other conditions (e.g., account up to date). If the calibrations/baselines are acceptable and there are no other conditions to prevent the test from occurring, event processing 754 can signal mobile chemical analysis device 700 to proceed. If not the test should not proceed, event processing 754 can signal mobile chemical analysis device 700 that recalibration or other action is required prior to continuing with the requested sample test.

Information retrieval 752 may receive from mobile chemical analysis device 700 test data and related metadata associated with a test. The test data and metadata may include x, y arrays (or other data structures) of raw voltage data, chemical concentration tables, user-provided metadata, environmental metadata, operational data, calibration factors used, baselines used, device identity, software versions and other data. Multidimensional aggregation 756 may aggregate data from a plurality of mobile chemical analysis devices 700 in one or more data stores along different dimensions of metadata.

Online analytical process 758 can analyze raw data and processed data to generate processed data and process processed data to generate further processed data. Processed data includes data determined during operation, and rules/models (such as machine learning models) that may be applied to raw data or processed data to generate further processed data and which may comprise, for example, models or rules. Online analytical process 758 match users to desired chemotype(s) that they have previously identified or that others like them have identified, determine relationships between phenotype (grow) impact on chemotype, determine if a chemical signature matches a strain, match chemotype to possible genotype(s) and phenotype(s), match chemical signature to previous chemical signatures for process control, QC/QA.

According to one embodiment, online analytical process 758 may match a user to a chemotype based on illness(es) and/or symptom(s) experienced by that user and the effective of that chemotype or similar chemotypes in alleviating those symptoms in other users.

Various predictive modelling 760, statistical inference 762, benchmarking 764, reporting 766 and data visualization 768 process may use the results of online analytical process 758.

Further embodiments described herein may be applied to other types of naturally occurring chemical compounds in plant samples, such as Kratom.

Routines, methods, steps, operations or portions thereof described herein can be implemented through control logic, including computer executable instructions stored on a computer readable medium, hardware, firmware or a combination thereof. The control logic can be adapted to direct an information processing device to perform a set of steps disclosed in the various embodiments. Some embodiments may be implemented by using software programming or code in one or more digital computers, by using application specific integrated circuits, programmable logic devices, field programmable gate arrays, optical, chemical, biological, quantum or nanoengineered systems, components and mechanisms. Based on the disclosure and teachings provided herein, a person of ordinary skill in the art will appreciate other ways and/or methods to implement the invention.

Computer executable instructions or code can be stored in a computer-readable medium and can be operated on by a processor to permit a computer to perform functions, steps, operations, methods, routines, operations or portions thereof described herein. Any suitable language. Different programming techniques can be employed such as procedural or object oriented.

Any particular step, operation, method, routine, operation or portion thereof can execute on a single computer processing device or multiple computer processing devices, a single computer processor or multiple computer processors. Data may be stored in a single storage medium or distributed through multiple storage mediums, and may reside in a single database or multiple databases (or other data storage). The sequence of operations described herein can be interrupted, suspended, or otherwise controlled by another process, such as an operating system, kernel, etc. The routines can operate in an operating system environment or as stand-alone routines.

A "computer-readable medium" may be any type of data storage medium that can store computer instructions, including, but not limited to read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, or semiconductor system, apparatus, system, device, or computer memory. The computer readable medium may include multiple computer readable media storing computer executable instructions, such as in a distributed system or instructions stored across an array.

A "processor" includes any hardware system, hardware mechanism or hardware component that processes data, signals or other information. A processor can include a system with a central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

It will be understood for purposes of this disclosure that a service or module is one or more computer devices, configured (e.g., by a computer process or hardware) to perform one or more functions. A service may present one or more interfaces which can be utilized to access these functions. Such interfaces include APIs, interfaces presented for a web services, web pages, remote procedure calls, remote method invocation, etc.

Embodiments can be implemented in a computer communicatively coupled to a network (for example, the Internet, an intranet, an internet, a WAN, a LAN, a SAN, etc.), another computer, or in a standalone computer. As is known to those skilled in the art, the computer can include a central processing unit ("CPU") or processor, memory (e.g., primary or secondary memory such as RAM, ROM, HD or other computer readable medium for the persistent or temporary storage of instructions and data) and one or more input/output ("I/O") device(s). The I/O devices can include a keyboard, monitor, printer, electronic pointing device (for example, mouse, trackball, stylus, etc.), touch screen or the like. In embodiments, the computer has access to at least one database on the same hardware or over the network.

As used herein, a term preceded by "a" or "an" (and "the" when antecedent basis is "a" or "an") includes both singular and plural of such term unless the context clearly dictates otherwise. Also, as used in the description herein, the meaning of "in" includes "in" and "on" unless the context clearly dictates otherwise.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," "in one embodiment."

Reference throughout this specification to "one embodiment," "an embodiment," or "a specific embodiment" or similar terminology means that a particular feature, structure, or characteristic described in connection with the embodiment is included in at least one embodiment and may not necessarily be present in all embodiments. Thus, respective appearances of the phrases "in one embodiment," "in an embodiment," or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention as related to cannabinoid and terpene testing.

Although the invention has been described with respect to specific embodiments thereof, these embodiments are merely illustrative, and not restrictive of the invention. The description herein of illustrated embodiments of the invention is not intended to be exhaustive or to limit the invention to the precise forms disclosed herein (and in particular, the inclusion of any particular embodiment, feature or function is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

In the foregoing specification, the invention has been described with reference to specific embodiments. However, one of ordinary skill in the art appreciates that various modifications and changes can be made without departing from the scope of the invention. Accordingly, the specification and figures are to be regarded in an illustrative rather than a restrictive sense, and all such modifications are intended to be included within the scope of invention.

What is claimed is:

1. A chemical analysis data system comprising:
a chemical analysis data server communicatively coupled to a network; and
a plurality of mobile chemical analysis devices communicatively coupled to the network, wherein the mobile chemical analysis devices are remote from the chemical analysis data server;
wherein each of the plurality of mobile chemical analysis devices is adapted to perform one or more physical analyses of a physical sample and to communicate data resulting from the physical analyses to the chemical analysis data server;
wherein the chemical analysis data server is adapted to perform one or more sample analyses on the data received from the mobile chemical analysis devices, generate one or more sample analysis reports, and communicate the one or more sample analysis reports to a user;
wherein each of the plurality of mobile chemical analysis devices is adapted to monitor one or more device parameters of the mobile chemical analysis device and to communicate the device parameters to the chemical analysis data server;
wherein the chemical analysis data server is adapted to aggregate the device parameters of the plurality of mobile chemical analysis devices and to perform one or more device analyses on the aggregated device parameters;
wherein the chemical analysis data server is adapted to perform multivariate analysis on the aggregated device parameters and to identify a fault condition of one of the mobile chemical analysis devices which is indicated by a corresponding parameter of the one of the mobile chemical analysis devices which is determined by the chemical analysis data server to be outside an acceptable range for the parameter based on the multivariate analysis of the aggregated device parameters;
wherein in response to identifying the fault condition, the chemical analysis data server is adapted to communicate control data to the corresponding one of the mobile chemical analysis devices; and
wherein the control data controls one or more aspects of the operation of the one of the mobile chemical analysis devices.

2. The chemical analysis data system of claim 1, wherein at least one of the plurality of mobile chemical analysis devices comprises a plurality of analytical device modules that are adapted to analyze a physical sample, wherein each of the analytical device modules performs a distinct type of sample analysis on the physical sample.

3. The chemical analysis data system of claim 1, further comprising, for at least one of the plurality of mobile chemical analysis devices, a user interface co-located with the mobile chemical analysis device, wherein the user interface is adapted to enable input of user-provided metadata associated with a sample on which the mobile chemical analysis device performs one or more physical analyses, wherein the user-provided metadata is communicated by the mobile chemical analysis device to the chemical analysis data server with the data resulting from the physical analyses.

4. The chemical analysis data system of claim 1, further comprising, for at least one of the plurality of mobile chemical analysis devices, a user interface co-located with the mobile chemical analysis device, wherein the user interface is adapted to receive data from the chemical analysis data server defining user instructions for preparing the physical sample or taking one or more actions to operate the mobile chemical analysis device.

5. The chemical analysis data system of claim 1, wherein the mobile chemical analysis device generates a unique identifier for each sample on which the mobile chemical analysis device performs one or more physical analyses, and wherein the unique identifier is communicated to the chemical analysis data server with the data resulting from the physical analyses.

6. A method implemented in a chemical analysis data system having a chemical analysis data server and a plurality of mobile chemical analysis devices communicatively coupled to a network, wherein the mobile chemical analysis devices are remote from the chemical analysis data server, the method comprising:
performing, by each of the plurality of mobile chemical analysis devices, one or more physical analyses of a corresponding physical sample;

communicating, by each of the plurality of mobile chemical analysis devices, data resulting from the corresponding physical analyses to the chemical analysis data server;

performing, by the chemical analysis data server, one or more sample analyses on the data received from the mobile chemical analysis devices;

generating, by the chemical analysis data server, one or more sample analysis reports;

wherein each of the plurality of mobile chemical analysis devices is adapted to monitor one or more device parameters of the mobile chemical analysis device, the method further comprising the chemical analysis data server: receiving the device parameters; aggregating the received device parameters of the plurality of mobile chemical analysis devices; and performing one or more device analyses on the aggregated device parameters; and wherein performing the one or more device analyses on the aggregated device parameters comprises the chemical analysis data server performing multivariate analysis on the aggregated device parameters; identifying a fault condition of one of the mobile chemical analysis devices which is indicated by a corresponding parameter of the one of the mobile chemical analysis devices which is determined by the chemical analysis data server to be outside an acceptable range for the parameter based on the multivariate analysis of the aggregated device parameters, and communicating control data to the corresponding one of the mobile chemical analysis devices in response to identifying the fault condition, wherein the control data controls one or more aspects of the operation of the one of the mobile chemical analysis devices.

7. The method of claim 6, wherein at least one of the plurality of mobile chemical analysis devices comprises a plurality of analytical device modules that are adapted to analyze a physical sample, the method further comprising performing, by each of the analytical device modules, a distinct type of sample analysis on the physical sample.

8. The method of claim 6, further comprising the chemical analysis data server receiving from at least one of the plurality of mobile chemical analysis devices, user-provided metadata associated with a sample on which the mobile chemical analysis device performs one or more physical analyses, wherein the user-provided metadata is provided by a user via a user interface co-located with the mobile chemical analysis device, wherein the user-provided metadata is received with the data resulting from the physical analyses.

9. The method of claim 6, further comprising the chemical analysis data server providing to at least one of the plurality of mobile chemical analysis devices instructions for preparing the physical sample or taking one or more actions to operate the mobile chemical analysis device, wherein the instructions are displayable to a user by a user interface co-located with the mobile chemical analysis device.

10. The method of claim 6, further comprising the chemical analysis data server receiving from each mobile chemical analysis device, for each sample on which the mobile chemical analysis device performs one or more physical analyses, a unique identifier for the sample generated by the mobile chemical analysis device.

11. A computer program product comprising at least one non-transitory computer readable medium storing instructions translatable by a computing device embodying a chemical analysis data system to perform:

communicating, by the chemical analysis data system, with each of a plurality of mobile chemical analysis devices;

receiving, by the chemical analysis data system, from each of the plurality of mobile chemical analysis devices data comprising results of one or more physical analyses of a corresponding physical sample;

performing, by the chemical analysis data system, one or more sample analyses on the results data received from the mobile chemical analysis devices;

generating, by the chemical analysis data system, one or more sample analysis reports; and communicating, by the chemical analysis data system, the one or more sample analysis reports to corresponding users;

receiving, by the chemical analysis data system, data for one or more device parameters of each of the mobile chemical analysis devices;

aggregating the received device parameters of the plurality of mobile chemical analysis devices; and performing one or more device analyses on the aggregated device parameters, wherein the chemical analysis data system performing the one or more device analyses on the aggregated device parameters comprises:

performing multivariate analysis on the aggregated device parameters, identifying a fault condition of one of the mobile chemical analysis devices which is indicated by a corresponding parameter of the one of the mobile chemical analysis devices which is determined by the chemical analysis data system to be outside an acceptable range for the parameter based on the multivariate analysis of the aggregated device parameters, and communicating control data to the corresponding one of the mobile chemical analysis devices in response to identifying the fault condition, wherein the control data controls one or more aspects of the operation of the one of the mobile chemical analysis devices.

12. The computer program product of claim 11, wherein receiving the data comprising results of the one or more physical analyses comprises receiving, from at least one of the plurality of mobile chemical analysis devices, results of a plurality of distinct types of sample analyses on the same physical sample.

13. The computer program product of claim 11, further comprising the chemical analysis data system receiving, from at least one of the plurality of mobile chemical analysis devices, user-provided metadata associated with a sample on which the mobile chemical analysis device performs one or more physical analyses, wherein the user-provided metadata is received via a user interface co-located with the mobile chemical analysis device, wherein the user-provided metadata is received with the data resulting from the physical analyses.

14. The computer program product of claim 11, further comprising the chemical analysis data system generating instructions for preparing the physical sample or taking one or more actions to operate the mobile chemical analysis device, wherein the instructions are provided by the chemical analysis data system to at least one of the plurality of mobile chemical analysis devices and are displayable to a user by a user interface co-located with the mobile chemical analysis device.

* * * * *